(12) United States Patent
Kawasaki (10) Patent No.: US 9,550,013 B2
(45) Date of Patent: Jan. 24, 2017

(54) MEDICAL GUIDE WIRE

(75) Inventor: Hironori Kawasaki, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 309 days.

(21) Appl. No.: 13/254,222

(22) PCT Filed: Feb. 9, 2010

(86) PCT No.: PCT/JP2010/051859
§ 371 (c)(1),
(2), (4) Date: Sep. 1, 2011

(87) PCT Pub. No.: WO2010/106848
PCT Pub. Date: Sep. 23, 2010

(65) Prior Publication Data
US 2011/0319872 A1    Dec. 29, 2011

(30) Foreign Application Priority Data

Mar. 19, 2009  (JP) ................................. 2009-067638
Sep. 15, 2009  (JP) ................................. 2009-212620

(51) Int. Cl.
*A61B 5/00*  (2006.01)
*A61L 31/02*  (2006.01)
*A61M 25/09*  (2006.01)

(52) U.S. Cl.
CPC ............. *A61L 31/022* (2013.01); *A61M 25/09* (2013.01); *A61M 2025/09091* (2013.01)

(58) Field of Classification Search
CPC  A61M 25/009; A61M 25/0012; A61M 25/09; A61M 25/09016; A61M 2025/09108; A61M 2025/09133; A61M 2025/09166; A61M 2025/09175

(Continued)

(56) References Cited

U.S. PATENT DOCUMENTS 5,147,317 A     9/1992  Shank et al.
5,234,003 A *   8/1993  Hall ............................. 600/585

(Continued)

FOREIGN PATENT DOCUMENTS

EP    1123714 A1    8/2001
EP    2014329 A1    1/2009

(Continued)

OTHER PUBLICATIONS

Japanese Office Action mailed Jan. 18, 2013 in Japanese patent application, 2009-212620.

(Continued)

*Primary Examiner* — Max Hindenburg
*Assistant Examiner* — Jonathan M Foreman
(74) *Attorney, Agent, or Firm* — Holtz, Holtz & Volek PC (57) ABSTRACT

A medical guide wire which has a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction and fixed to the core wire at at least the front end portion and rear end portion thereof. The outside diameter of the proximal end-side large-diameter portion of the core wire and the outside diameter of coil of the coil spring are each at most 0.012 inch. The front end portion of the coil spring is fixed to the core wire by gold-containing solder. The length of a distal end portion stiffened by the gold-containing solder is 0.1 to 0.5 mm. The medical guide wire is high in fixing strength of the coil spring to the core wire and can shorten a shaping length compared with a conventional medical guide wire.

15 Claims, 5 Drawing Sheets (58) Field of Classification Search
USPC .............. 600/433, 434, 435, 585; 604/164.13
See application file for complete search history.

(56) References Cited

U.S. PATENT DOCUMENTS

| | | | |
|---|---|---|---|
| 6,251,086 B1 | 6/2001 | Cornelius et al. | |
| 6,669,652 B2 | 12/2003 | Anderson et al. | |
| 7,170,100 B2* | 1/2007 | Erchak et al. | 257/88 |
| 7,637,874 B2 | 12/2009 | Terashi et al. | |
| 7,993,286 B2* | 8/2011 | Reynolds et al. | 600/585 |
| 2007/0249964 A1 | 10/2007 | Richardson et al. | |
| 2007/0282225 A1 | 12/2007 | Terashi et al. | |
| 2008/0033530 A1 | 2/2008 | Zberg et al. | |
| 2008/0097248 A1* | 4/2008 | Munoz et al. | 600/585 |
| 2008/0146967 A1* | 6/2008 | Richardson et al. | 600/585 |
| 2008/0281230 A1 | 11/2008 | Kinoshita et al. | |
| 2008/0292493 A1 | 11/2008 | Lee et al. | |
| 2011/0319872 A1 | 12/2011 | Kawasaki | |

FOREIGN PATENT DOCUMENTS

| | | |
|---|---|---|
| JP | 2003-299739 A | 10/2003 |
| JP | 2006-020942 A | 1/2006 |
| JP | 2006-055245 A | 3/2006 |
| JP | 2006-223728 A | 8/2006 |
| JP | 2007-111118 A | 5/2007 |
| JP | 4354523 B1 | 9/2007 |
| JP | 2008-307367 A | 12/2008 |
| JP | 2010-268888 A | 2/2010 |
| JP | 2010-214054 A | 9/2010 |
| WO | WO 2008/022126 A1 | 2/2008 |
| WO | WO 2010/134364 A1 | 11/2010 |

OTHER PUBLICATIONS

Chinese Office Action mailed Feb. 5, 2013 in Chinese patent application 201080010498.X.
International Preliminary Report on Patentability and Written Opinion of the International Searching Authority for PCT/JP 2010/051859 dated Mar. 19, 2010.
Second Office Action which issued on Sep. 30, 2013 for corresponding Chinese application 201080010498.X (including an English-language translation).
First Examination Report dated Mar. 13, 2014, which issued in the corresponding Indian Application No. 1725/MUMNP/2011.
Copending U.S. Appl. No. 13/265,947.
Supplementary European Search Report for EP 10 75 3343 dated Feb. 10, 2014.
D.R. Olsen et al., "Properties of Die Bond Alloys Relating to Thermal Fatigue", *IEEE Transactions on Components, Hybrids, and Manufacturing Technology*, vol. CHMT-2, No. 2, Jun. 1979.
Abstract XP002719332 of JP H0 7234338, Hitachi Ltd., Sep. 5, 1995.
Thomson Scientific Abstract of JP 2006-020942, Terumo Corp., Jan. 26, 2006.
Thomson Scientific Abstract of JP 2006-22378, Pyorax Medical Device, Aug. 31, 2006.
Third Office Action which issued on Mar. 27, 2014 for corresponding Chinese application 201080010498.X (including an English-language translation thereof).
Jacobson, et al. (2005), "Principles of Brazing", ASM International. Sect 5.4. pp. 197-200. Retrieved from <http://app.knovel.com/hotlink/toc/id:kpPB000004/principles-brazing> on Jan. 12, 2015.
English-language machine translation of JP 2006-020942.
Chinese Office Action dated Aug. 12, 2014, issued in counterpart Chinese Application No. 201080010498.X.
Australian Office Action dated Oct. 30, 2014, issued in counterpart Australian Application No. 2010225987.

* cited by examiner

MEDICAL GUIDE WIRE

CROSS-REFERENCE TO RELATED APPLICATION

This application is a United States national phase application of International Application PCT/JP2010/051859 filed Feb. 9, 2010.

TECHNICAL FIELD

The present invention relates to a medical guide wire having a coil spring installed on an outer periphery of a distal end-side small-diameter portion of a core wire, and more particularly to a medical guide wire which is high in fixing strength of a coil spring to a core wire, can more shorten a shaping length in a shaping operation at a distal end portion than a conventional one and is excellent in operability within a micro-channel of CTO lesion.

BACKGROUND ART

A guide wire for guiding a medical instrument such as a catheter to a predetermined position in a body cavity such as a blood vessel is required to have flexibility at its distal end portion.

Therefore, there is known a guide wire in which the outside diameter of an distal end portion of a core wire is made smaller than that of its proximal end portion, and a coil spring is installed on an outer periphery of the distal end portion (distal end-side small-diameter portion) of the core wire, thereby intending to improve the flexibility of the distal end portion (see, for example, Patent Literature 1).

In order to install the coil spring on the outer periphery of the distal end-side small-diameter portion of the core wire, both front end portion and rear end portion of the coil spring are generally fixed to the core wire by solder.

Here, Ag—Sn solder is used as the solder for fixing both front end portion and rear end portion of the coil spring to the core wire because of its low melting point and easy handling.

The solder penetrated into the interior of the coil at both front end portion and rear end portion of the coil spring comes into contact with the outer peripheral surface of the core wire, whereby the coil spring is fixed to the core wire.

In addition, a distal end tip is formed by any other solder than the solder penetrated into the interior of the coil at the front end portion of the coil spring.

In order to ensure the fixing ability of the coil spring to the core wire, however, it is necessary to sufficiently penetrate the solder into the interior of the coil at the front end portion of the coil spring, which is fixed to a distal end portion of the core wire, which has a minimum outside diameter. Specifically, it is necessary to penetrate the solder (Ag—Sn solder) into the interior of the coil in a range corresponding to about 6 pitches to about 8 pitches of the coil spring.

A portion (including the distal end tip formed by the solder) stiffened by the solder filled into the interior of the coil is formed at the distal end portion of the guide wire produced in this manner.

The length (length correspond to the distal end tip and about 6 pitches to about 8 pitches of the coil) of this distal-end stiff portion is about 0.8 to 1.1 mm.

In order to achieve low invasiveness in a patient, it has been recently desired to miniaturize medical instruments.

With this desire, there has been a demand for making the diameter of a guide wire small, and so the present inventors have come to develop a guide wire having a smaller wire diameter (0.010 inch) than that (0.014 inch) of a conventional one.

The guide wire of 0.010 inch can greatly contribute to the miniaturization of medical instruments such as catheters.

In addition, this guide wire is also good in operability upon accessing, for example, a micro-channel in CTO (chronic total occlusion) lesion.

CITATION LIST

Patent Literature

Patent Literature 1: Japanese Patent Application Laid-Open No. 2003-299739

SUMMARY OF INVENTION

Technical Problem

The guide wire inserted into the micro-channel in the CTO lesion is required to more improve the operability. For example, it is desired to reduce a frictional resistance upon operation within the micro-channel. However, there is a limit to the reduction of the frictional resistance by making the wire diameter of the guide wire small.

By the way, an operator shapes (shaping) a distal end portion of a guide wire into a bent portion when the guide wire is inserted into the micro-channel.

Figure 5:
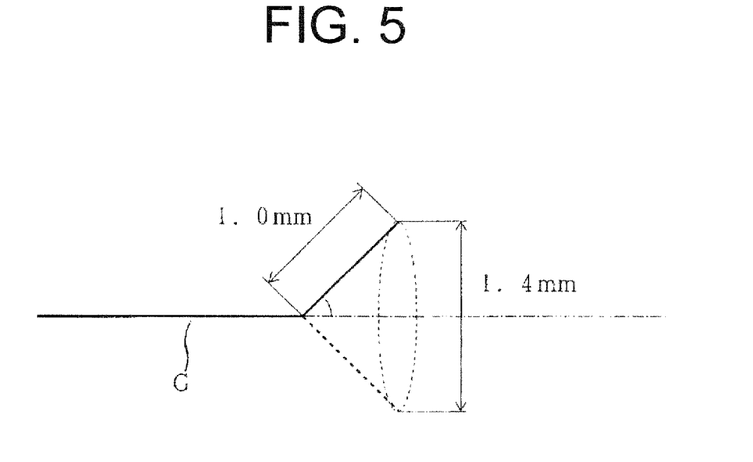
FIG. 5 is an explanatory view typically illustrating the state that the distal end portion of the guide wire has been shaped.

For example, when the shaping is conducted by bending the guide wire G by 45° at a position 1.0 mm away from the distal end thereof as illustrated in FIG. 5, and rotational torque is applied to the guide wire on its proximal end side, the distal end of the guide wire comes to be rotated on a circumference having a diameter of about 1.4 mm.

This shaping operation greatly affects the operability of the guide wire within the micro-channel.

The diameter (operation area) of a circle drawn by the rotation of the distal end of the guide wire is preferably made small from the viewpoint of, for example, reducing the frictional resistance within the micro-channel. It is thus necessary to make a shaping length (length of the bent portion on the distal end side) as short as possible, specifically, not more than 0.7 mm.

However, the conventional guide wire has the above-described distal-end stiff portion, and so the shaping length cannot be set to 1.0 mm or less, thereby failing to sufficiently reduce the frictional resistance.

Incidentally, if the length of the distal-end stiff portion is shortened by narrowing a range where the solder (Ag—Sn solder) is penetrated, the fixing ability of the coil spring to the core wire cannot be sufficiently ensured, and the core wire in a state inserted into the coil spring is pulled out from the coil spring when tensile force is applied between the core wire and the coil spring.

The present invention has been made on the basis of the foregoing circumstances.

The first object of the present invention is to provide a medical guide wire which is high in fixing strength of a coil spring to a core wire and can shorten a shaping length compared with a conventional one.

The second object of the present invention is to provide a medical guide wire excellent in operability within a microchannel of CTO lesion.

Solution to Problem

The medical guide wire according to the present invention is a medical guide wire comprising a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction and fixed to the core wire at least the front end portion and rear end portion thereof, wherein the outside diameter of the proximal end-side large-diameter portion of the core wire and the outside diameter of coil of the coil spring are each at most 0.012 inch, the front end portion of the coil spring is fixed to the core wire by gold-containing solder, and the length of a distal end portion (distal-end stiff portion) stiffened by the gold-containing solder is 0.1 to 0.5 mm.

Here, "the gold-containing solder" includes Au alloy solder such as Au—Sn solder, Au—Ge solder, Au—Si solder, Au—In solder and Au—Sb solder, and Au solder.

The medical guide wire according to a preferred embodiment of the present invention is a medical guide wire comprising a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction and fixed to the core wire at least the front end portion and rear end portion thereof, wherein the outside diameter of the proximal end-side large-diameter portion of the core wire and the outside diameter of coil of the coil spring are each at most 0.012 inch, the front end portion of the coil spring is fixed to the core wire by Au—Sn solder, and the length of a distal end portion (distal-end stiff portion) stiffened by the Au—Sn solder is 0.1 to 0.5 mm.

The medical guide wire according to another preferred embodiment of the present invention is a medical guide wire comprising a core wire having a distal end-side small-diameter portion and a proximal end-side large-diameter portion having a larger outside diameter than the outside diameter of the distal end-side small-diameter portion, and a coil spring installed on an outer periphery of the distal end-side small-diameter portion of the core wire along an axial direction and fixed to the core wire at least the front end portion and rear end portion thereof, wherein the outside diameter of the proximal end-side large-diameter portion of the core wire and the outside diameter of coil of the coil spring are each at most 0.012 inch, the front end portion of the coil spring is fixed to the core wire by Au—Ge solder, and the length of a distal end portion (distal-end stiff portion) stiffened by the Au—Ge solder is 0.1 to 0.5 mm.

Here, "the distal-end stiff portion." means a front (distal) end portion of the coil spring (guide wire), which cannot be freely bent due to the solder penetrated into the interior of the coil. When a distal end tip is formed by the solder, this distal end tip also becomes a part of the distal-end stiff portion.

In addition, "the length of the distal-end stiff portion" means a length of the guide wire from the distal end of the guide wire to the rear end of the solder penetrated into the interior of the coil in an axial direction.

In the medical guide wire according to the present invention, the following embodiments are preferred.

(1) The outside diameter of the proximal end-side large-diameter portion of the core wire and the outside diameter of coil of the coil spring are each at most 0.010 inch, particularly, 0.006 to 0.010 inch.

(2) The coil pitch of the coil spring at its front end portion is 1.0 to 1.8 times as much as the wire diameter of the coil, and the Au—Sn solder or Au—Ge solder penetrates into the interior of the coil in a range (length) corresponding to 1 to 3 pitches of the coil spring.

(3) A resin is filled into the interior (space surrounded by the outer periphery of the distal end-side small-diameter portion of the core wire and the inner periphery of the coil spring) of the coil spring, a resin layer by the resin is formed on the outer periphery of the coil spring, a hydrophilic resin layer is laminated and formed on the surface of the resin layer, and a water-repellent resin layer is formed on the surface of the core wire.

(4) The coil spring is composed of a front end-side densely-coiled portion whose coil pitch is 1.0 to 1.8 times as much as the wire diameter of the coil, and a rear end-side roughly-coiled portion whose coil pitch exceeds 1.8 times as much as the wire diameter of the coil.

(5) An intermediate portion of the coil spring, including the front end-side densely-coiled portion and the rear end-side roughly-coiled portion, is fixed to the core wire by the Au—Sn solder or Au—Ge solder.

(6) The core wire is composed of stainless steel.

Advantageous Effects of Invention

According to the medical guide wires of the present invention, the gold-containing solder, preferably, Au—Sn solder or Au—Ge solder is used as solder for fixing the front end portion of the coil spring to the core wire, so that the fixing strength of the coil spring to the core wire can be made sufficiently high (higher than the breaking strength of the distal end-side small-diameter portion of the core wire) though the length of the distal-end stiff portion is as short (narrow in a region fixed by the solder) as 0.1 to 0.5 mm, and so the core wire is not pulled out from the coil spring when tensile force is applied to the core wire in a state inserted into the coil spring.

In addition, since the length of the distal-end stiff portion is as short as 0.1 to 0.5 mm, the shaping length (length of the bent portion on the distal end side) can be made short (not more than 0.7 mm). As a result, frictional resistance upon operation within the micro-channel can be sufficiently reduced.

Further, a treatment in a narrow region, which has been unable to be conducted by using the conventional guide wire, also becomes feasible.

The medical guide wires according to the present invention are excellent in operability within the micro-channel of CTO lesion because of the wire diameter as fine as 0.012 inch or less, high fixing strength owing to the gold-containing solder and the distal-end stiff portion as short as 0.1 to 0.5 mm.

According to the medical guide wire of the embodiment (3), the resin is filled into the interior of the coil spring, whereby the core wire and the coil spring can be integrated with each other to especially improve the torque transferability and operability of the guide wire.

In addition, since the hydrophilic resin layer is laminated and formed on the outer periphery of the coil spring through a resin layer by the same resin as that filled into the interior of the coil spring, the hydrophilic resin layer can be surely fixed to stably develop the lubricating ability by the hydrophilic resin.

Further, the water-repellent resin layer is formed on the surface of the core wire, whereby a blood of a patient can be prevented from coming into contact with a metal making up the core wire to cause an allergy, and the adhesion of the blood can be surely prevented by the water-repellent resin layer. In addition, lubricating ability to other medical instruments can be developed.

According to the medical guide wire of the embodiment (4), good contrasting characteristic for X-ray (visibility) can be developed at the front end portion (front end-side densely-coiled portion) of the coil spring.

According to the medical guide wire of the embodiment (5), a boundary region between the front end-side densely-coiled portion and the rear end-side roughly-coiled portion, where stress concentration is easy to occur, is fixed by the Au—Sn solder or Au—Ge solder high in fixing ability, so that the fixing strength of the coil spring to the core wire can be more improved.

DESCRIPTION OF EMBODIMENTS

Figure 1:
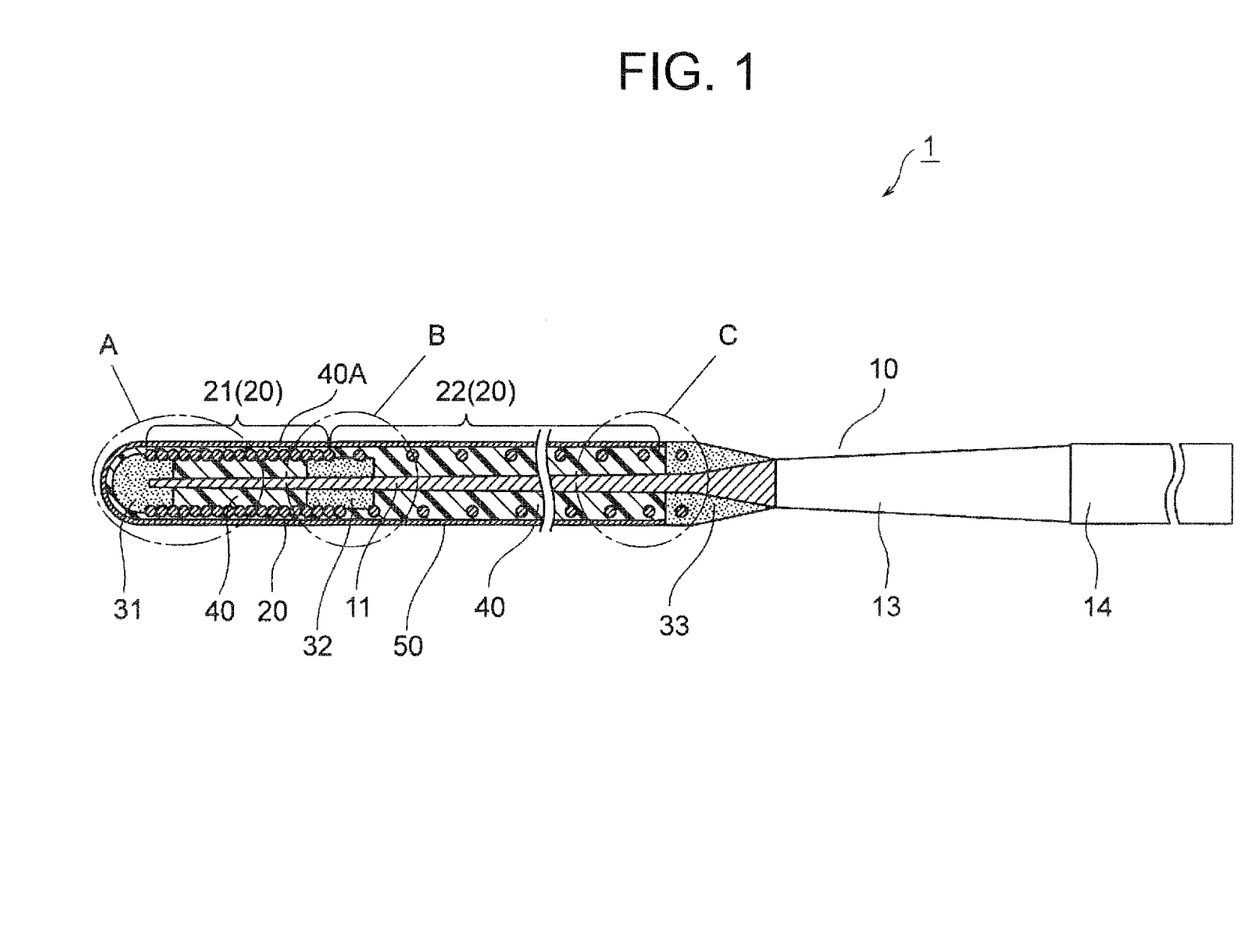
FIG. 1 is a side elevation, partly broken away, illustrating a guide wire according to an embodiment of the present invention.

The guide wire illustrated in FIG. 1 has a core wire 10 and a coil spring 20.

The core wire 10 has a distal end-side small-diameter portion 11 subjected to taper machining so as to expand its diameter towards proximal direction, a tapered portion 13 whose diameter expands towards proximal direction, and a proximal end-side large-diameter portion 14.

The distal end-side small-diameter portion 11, the tapered portion 13 and the proximal end-side large-diameter portion 14 are integrally formed by the same wire material, for example, a round bar member.

The sectional surfaces (cross sections) of the tapered portion 13 and the proximal end-side large-diameter portion 14 are substantially circular.

The sectional surface on a proximal end side of the distal end-side small-diameter portion 11 is substantially circular. However, the wire material may be compressed into a plate form on a distal end side of the distal end-side small-diameter portion 11, and the sectional surface thereof is substantially rectangular in that case.

No particular limitation is imposed on the material of the core wire 10. As examples thereof, however, may be mentioned metals such as stainless steel (for example, SUS316 and SUS304), gold, platinum, aluminum, tungsten, tantalum and alloys thereof. In this embodiment, the core wire is composed of stainless steel.

A water-repellent resin layer is formed on the outer periphery of the core wire 10.

As a resin forming the water-repellent resin layer, may be used all resins medically used and having water repellency, and fluororesins such as PTFE may be mentioned as preferable resins.

Figure 2:
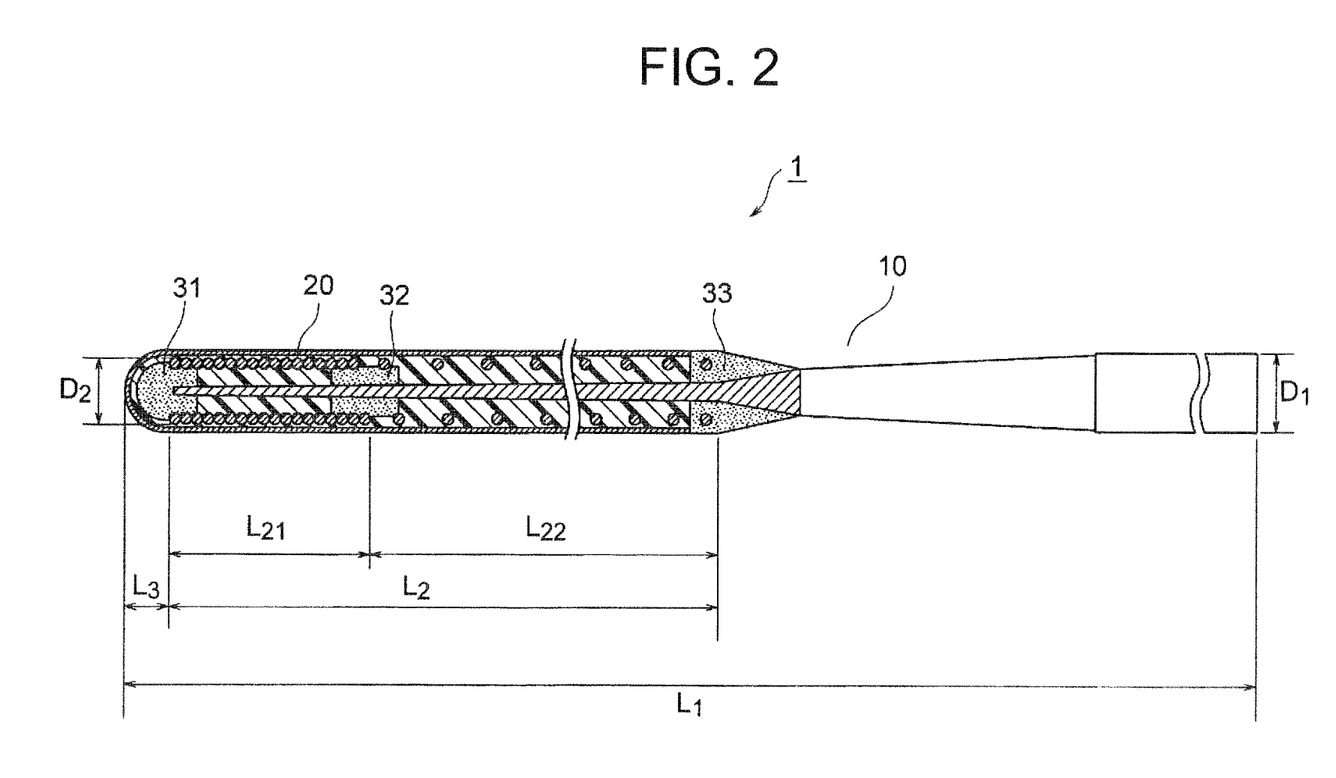
FIG. 2 is a side elevation (drawing for explaining dimensions), partly broken away, illustrating the guide wire according to the embodiment of the present invention.

As illustrated in FIG. 2, the overall length ($L_1$) of the guide wire 1 is, for example, 1,500 to 3,000 mm, and is 1,780 mm as a preferable example.

The outside diameter ($D_1$) of the proximal end-side large-diameter portion 14 is generally 0.012 inch (0.305 mm) or less, preferably 0.010 inch (0.254 mm) or less, more preferably 0.006 to 0.010 inch, and is 0.010 inch as a preferable example.

The fact that the outside diameter ($D_1$) of the proximal end-side large-diameter portion 14 is 0.012 inch or less can contribute to the miniaturization of medical instruments such as catheters used together with the guide wire according to the present invention and in turn, to low invasiveness.

No particular limitation is imposed on the maximum outside diameter of the distal end-side small-diameter portion 11 so far as it is smaller than the inside diameter of the coil spring 20. However, the outside diameter is about ⅕ to ⅗ of the outside diameter ($D_1$) of the proximal end-side large-diameter portion 14.

The coil spring 20 making up the guide wire 10 is installed on an outer periphery of the distal end-side small-diameter portion 11 of the core wire 10 along an axial direction.

The coil spring 20 is formed by one wire material and composed of a front end-side densely-coiled portion 21 whose coil pitch is 1.0 to 1.8 times as much as the wire diameter of the coil, and a rear end-side roughly-coiled portion 22 whose coil pitch exceeds 1.8 times as much as the wire diameter of the coil, and a radiopaque region is formed by the front end-side densely-coiled portion 21 and a distal end tip which will be described subsequently.

The coil pitch at the front end-side densely-coiled portion 21 is 1.0 to 1.8 times as much as the wire diameter of the coil, and is 1.0 time as a preferable example.

The coil pitch at the rear end-side roughly-coiled portion 22 is 1.8 to 2.5 times as much as the wire diameter of the coil, and is 2.0 time as a preferable example.

The coil pitch is changed between the front end side and the rear end side as described above, whereby good contrasting characteristic for X-ray (visibility) can be developed at the front end-side densely-coiled portion 21.

When the pitch of the coil spring is made equal over the whole region, lowering of the visibility is incurred because the radiopaque region becomes long.

In FIG. 2, the length ($L_2$) of the coil spring 20 is, for example, 30 to 800 mm, and is 115 mm as a preferable example.

The length ($L_{21}$) of the front end-side densely-coiled portion 21 is, for example, 10 to 50 mm, and is 30 mm as a preferable example.

The length ($L_{22}$) of the rear end-side roughly-coiled portion 22 is, for example, 20 to 750 mm, and is 85 mm as a preferable example.

The length ($L_3+L_2$) from the distal end of the guide wire 1 to the rear end of the coil spring 20 is, for example, 30 to 800 mm, and is 115.2 mm as a preferable example.

The length ($L_3+L_{21}$) from the distal end of the guide wire 1 to the rear end of the front end-side densely-coiled portion 21 is, for example, 10 to 50 mm, and is 30.2 mm as a preferable example.

The outside diameter ($D_2$) of coil of the coil spring 20 is generally 0.012 inch (0.305 mm) or less, preferably 0.010 inch (0.254 mm) or less, more preferably 0.006 to 0.010 inch, and is 0.010 inch as a preferable example.

The fact that the outside diameter ($D_1$) of the proximal end-side large-diameter portion 14 of the core wire 10 is 0.012 inch or less, and the outside diameter ($D_2$) of coil of the coil spring 20 is also 0.012 inch or less makes the operability upon accessing a micro-channel (for example, lubricating ability in the micro-channel) excellent.

No particular limitation is imposed on the outside diameter of the wire material forming the coil spring 20. However, the outside diameter thereof is preferably 30 to 90 μm, and is 60 μm as a preferable example.

As example of the material of the coil spring 20, may be mentioned materials (radiopaque materials) good in contrasting characteristic for X-ray, such as platinum, platinum alloys (for example, Pt/W=92/8), gold, gold-copper alloys, tungsten and tantalum.

In the guide wire according to the present invention, the front end portion, rear end portion and intermediate portion (boundary region between the front end-side densely-coiled portion 21 and the rear end-side roughly-coiled portion 22) of the coil spring 20 are respectively fixed to the outer periphery of the distal end-side small-diameter portion 11 of the core wire 10 by solder.

Figure 3:
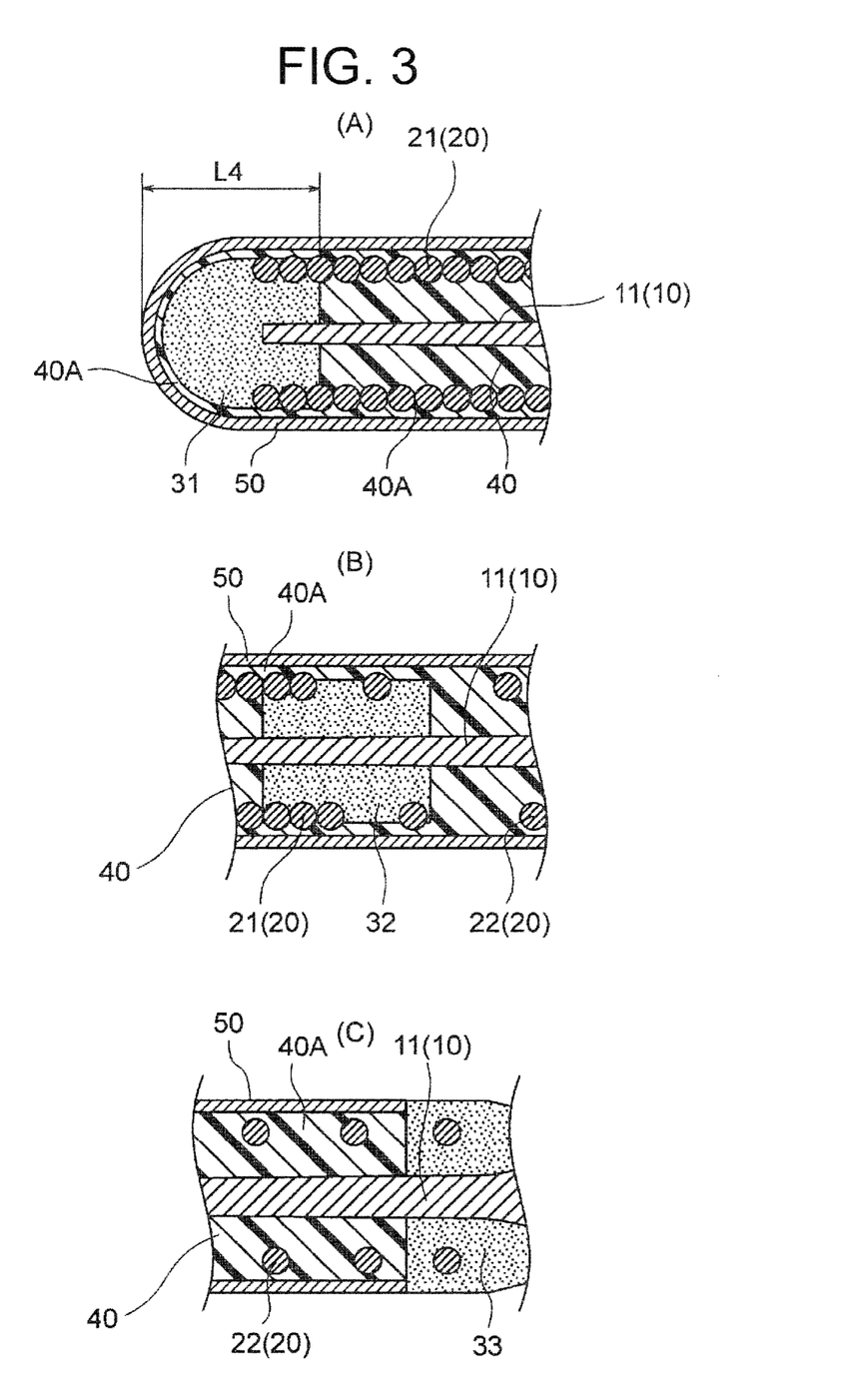
FIG. 3 is a partly enlarged view of FIG. 1, in which (A) is a detailed view of an A portion, (B) is a detailed view of a B portion, and (C) is a detailed view of a C portion.

As illustrated in FIG. 1 and FIG. 3(A), the front end portion of the coil spring 20 is fixed to the core wire 10 by the Au—Sn solder 31.

In short, the Au—Sn solder 31 penetrates into the interior of the coil spring 20 and comes into contact with the outer periphery of the core wire 10 (distal end-side small-diameter portion 11), whereby the front end portion of the coil spring 20 is fixed to the core wire 10 (distal end-side small-diameter portion 11).

As illustrated in FIG. 3(A), the Au—Sn solder 31 penetrates into the interior of the coil in a range corresponding to 2 pitches of the coil spring 20.

In addition, a substantially semispherical distal end tip is formed by any other Au—Sn solder 31 than the solder penetrated into the interior of the coil spring 20 at the front end portion of the coil spring 20.

A distal-end stiff portion (stiff portion by the front end portion of the coil spring 20 that has been unable to be freely bent due to the Au—Sn solder 31 penetrated into the interior of the coil, and the distal end tip formed by the Au—Sn solder 31) by the Au—Sn solder 31 is thereby formed at the distal end portion of the guide wire according to this embodiment.

The length (length from the distal end of the guide wire 1 to the rear end of the Au—Sn solder 31 penetrated into the interior of the coil) ($L_4$) of this distal-end stiff portion is about 0.3 to 0.4 mm.

In the guide wire according to the present invention, the length of the distal-end stiff portion is 0.1 to 0.5 mm.

If the length of the distal-end stiff portion is less than 0.1 mm, the fixing ability of the coil spring to the core wire cannot be sufficiently ensured.

If the length of the distal-end stiff portion exceeds 0.5 mm on the other hand, a shaping length (outside length ($L_{52}$) which will be described subsequently) cannot be set to 0.7 mm or less.

In order to set the length of the distal-end stiff portion to 0.1 to 0.5 mm in the guide wire according to the present invention, it is preferable that the coil, pitch of the front end portion of the coil spring is 1.0 to 1.8 times as much as the wire diameter of the coil, and the Au—Sn solder penetrates into the interior of the coil in a range corresponding to 1 to 3 pitches of the coil spring.

The medical guide wire according to this embodiment has a feature in that the Au—Sn solder is used as the solder for fixing the front end portion of the coil spring to the core wire.

The Au—Sn solder used in the present invention is composed of, for example, an alloy of 75-80% by mass of Au and 25 to 20% by mass of Sn.

Stainless steel is fixed to platinum (alloy) with the Au—Sn solder, whereby about 2.5 times of fixing strength (tensile strength) can be obtained compared with a case where they are fixed with the Ag—Sn solder.

Therefore, even when the length of the distal-end stiff portion is as short as 0.1 to 0.5 mm (even when the penetration range of the solder is 1 to 3 times as much as the coil pitch), the fixing strength of the coil spring 20 to the core wire 10 can be made sufficiently high. Specifically, the fixing strength can be made higher than tensile break strength at the distal end-side small-diameter portion 11 of the core wire 10. Therefore, even when tensile force is applied between the coil spring 20 and the core wire 10, the core wire 10 can be prevented from being pulled out from the coil spring 20.

In addition, the Au—Sn solder is excellent in contrasting characteristic for X-ray compared with the Ag—Sn solder.

Further, the Au—Sn solder is also excellent in corrosion resistance to blood and body fluid compared with the Ag—Sn solder.

As illustrated in FIG. 1 and FIG. 3(B), an intermediate portion of the coil spring 20, including a boundary region between the front end-side densely-coiled portion 21 and the rear end-side roughly-coiled portion 22, is fixed to the core wire 10 by Au—Sn solder 32.

In short, the Au—Sn solder 32 penetrates into the interior of the coil spring 20 and comes into contact with the outer periphery of the core wire 10 (distal end-side small-diameter portion 11), whereby the intermediate portion of the coil spring 20 is fixed to the core wire 10 (distal end-side small-diameter portion 11).

The boundary region between the front end-side densely-coiled portion 21 and the rear end-side roughly-coiled portion 22 is easy to cause stress concentration. The intermediate portion including this boundary region is fixed by the Au—Sn solder high in fixing ability, whereby the fixing strength of the coil spring 20 can be more improved.

As illustrated in FIG. 1 and FIG. 3(C), the rear end portion of the coil spring 20 is fixed to the core wire 10 by Ag—Sn solder 33.

In short, the Ag—Sn solder 33 penetrates into the interior of the coil spring 20 and comes into contact with the outer periphery of the core wire 10 (distal end-side small-diameter portion 11), whereby the rear end portion of the coil spring 20 is fixed to the core wire 10 (distal end-side small-diameter portion 11).

Since the outside diameter of the portion, to which the rear end portion of the coil spring 20 is fixed, in the distal end-side small-diameter portion 11 of the core wire 10 is larger (relatively larger in fixing area) than the outside diameter of the portion (distal end), to which the front end portion of the coil spring 20 is fixed, the Ag—Sn solder low in fixing ability compared with the Au—Sn solder can be used.

As illustrated in FIG. 1 to FIG. 3, in the guide wire according to this embodiment, a cured resin 40 is filled into the interior of the coil spring 20, and the outer periphery of the coil spring 20 and the distal end tip are covered with a resin layer 40A by this cured resin 40.

A hydrophilic resin layer 50 is laminated and formed on the surface of this resin layer 40A.

The cured resin 40 is filled into the interior of the coil spring 20, whereby the core wire 10 is integrated with the coil spring 20, and the torque transferability of the guide wire is especially improved to surely transfer rotational torque transferred from the proximal end-side large-diameter portion 14 of the core wire 10 to the distal end of the coil spring 20 integrated with the distal end-side small-diameter portion 11.

In addition, the hydrophilic resin layer 50 is formed on the outer periphery of the coil spring 20 through the resin layer 40A (primer layer), so that this hydrophilic resin layer 50 can be firmly fixed to stably develop the lubricating ability by the hydrophilic resin.

Here, the cured resin 40 filled into the interior of the coil spring 20 and forming the resin layer 40A covering the outer periphery of the coil spring 20 preferably has good adhesive property to both coil spring 20 and hydrophilic resin, and as specific examples thereof, may be mentioned cured products of photo-setting resins or thermosetting resins such as urethane-acrylate resins, polyurethane resins, silicone resins, epoxy resins, acrylic resins and nylon resins.

The film thickness of the resin layer 40A covering the outer periphery of the coil spring 20 and the distal end tip is, for example, 1 to 100 μm, preferably 3 to 10 μm.

As a resin forming the hydrophilic resin layer laminated and formed on the surface of the resin layer 40A, may be used all resins used in the field of medical instruments.

The film thickness of the hydrophilic resin layer 50 is, for example, 1 to 30 μm, preferably 3 to 19 μm.

As examples of a method for filling the cured resin 40 and forming the resin layer 40A and a method for laminating and forming the hydrophilic resin layer 50, may be mentioned a method of immersing the coil spring 20 installed on the core wire 10 in a curable resin, thereby filling the curable resin into the interior of the coil spring 20 and forming a resin layer on the surface of the coil spring 20, and thermosetting or photo-setting this resin to form the cured resin 40 (resin layer 40A), and a method of applying a hydrophilic resin to the surface of the resin layer 40A by a proper means.

According to the guide wire 1 of this embodiment, the Au—Sn solder is used as the solder for fixing the front end portion of the coil spring 20 to the core wire 10, so that the fixing strength of the coil spring to the core wire (distal end-side small-diameter portion 11) is sufficiently high though the outside diameter of the proximal end-side large-diameter portion 14 of the core wire 10 is as fine as 0.012 inch or less, and the length of the distal-end stiff portion is as short as 0.3 to 0.4 mm, and so the core wire 10 is not pulled out from the coil spring 20 even when tensile force is applied between the coil spring 20 and the core wire 10.

In addition, the shaping length can be shortened because the length of the distal-end stiff portion is as short as 0.3 to 0.4 mm. As a result, frictional resistance upon operation within a micro-channel can be sufficiently reduced. In addition, a treatment in a narrow region, which has been unable to be conducted by using the conventional guide wire, also becomes feasible.

Further, the cured resin 40 is filled into the interior of the coil spring 20, so that the core wire 10 can be integrated with the coil spring 20, and the torque transferability and operability of the guide wire 1 can be especially improved.

Furthermore, the hydrophilic resin layer 50 is laminated and formed on the outer periphery of the coil spring 20 through the resin layer 40A by the cured resin 40, so that the lubricating ability by the hydrophilic resin can be stably developed.

In addition, the coil spring 20 is composed of the front end-side densely-coiled portion 21 and the rear end-side roughly-coiled portion 22, so that good contrasting characteristic for X-ray (visibility) can be developed at the front end-side densely-coiled portion 21.

Figure 4:
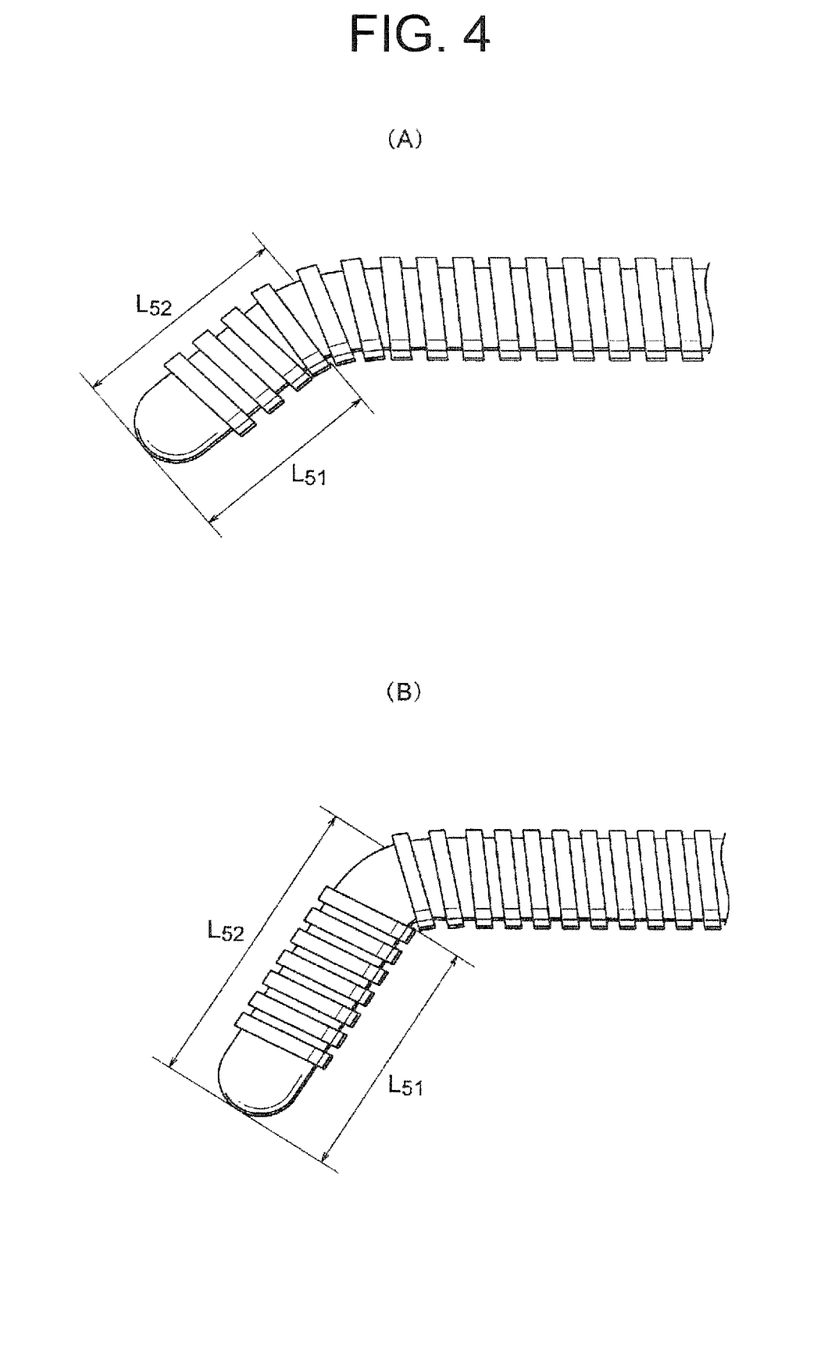
FIG. 4 is a side elevation illustrating a state that the distal end portion of the guide wire has been shaped.

FIG. 4(A) illustrate a state that the distal end portion of the guide wire (outside diameter of the coil spring=0.010 inch) according to the present invention has been shaped. The length of the distal-end stiff portion of this guide wire is 0.35 mm (the penetration range of the Au—Sn solder corresponds to 2 pitches of the coil spring), and the shaping length is 0.32 mm for inside length ($L_{51}$) and 0.53 mm for outside length ($L_{52}$).

FIG. 4(B) illustrate a state that the distal end portion of the conventional guide wire (outside diameter of the coil spring=0.010 inch) has been shaped. The length of the distal-end stiff portion of this guide wire is 0.8 mm (the penetration range of the Ag—Sn solder corresponds to 6 pitches of the coil spring), and the shaping length is 0.82 mm for inside length ($L_{51}$) and 1.01 mm for outside length ($L_{52}$).

The embodiment that the Au—Sn solder is used as the solder for fixing the front end portion and intermediate portion of the coil spring to the core wire has been described above. However, the same effect as in the case where the Au—Sn solder is used can be exhibited even by using other gold-containing solder in place of the Au—Sn solder.

As examples of other gold-containing solder than the Au—Sn, may be mentioned Au alloy solder such as Au—Ge solder, Au—Si solder, Au—In solder and Au—Sb solder, and Au solder.

EXAMPLES

Example 1

(1) Preparation of Guide Wire

A coil spring was installed on a distal end-side small-diameter portion of a core wire (core wire composed of stainless steel coated with PTFE) the outside diameter of a proximal end-side large-diameter portion of which was 0.010 inch to prepare 13 guide wires of such a structure as illustrated in FIG. 1 to FIG. 3 according to the present invention.

Here, the coil springs used were such that the outside diameter ($D_2$) of the coil is 0.010 inch, the length ($L_2$) is 115 mm, the length ($L_{21}$) of a front end-side densely-coiled portion (the coil pitch is 1.0 time as much as the wire diameter of the coil) is 30 mm, and the length ($L_{22}$) of a rear end-side roughly-coiled portion (the coil pitch is 2.0 times as much as the wire diameter of the coil) is 85 mm.

A front end portion and an intermediate portion of the coil spring were fixed to the core wire with Au—Sn solder, and a rear end portion of the coil spring was fixed to the core wire with Ag—Sn solder.

In each of the 13 guide wires, the number (in Table 1, abbreviated as "Number of pitches") of pitches a coil portion corresponding to a region (length) where the solder penetrated into the interior thereof was set to any of 1 to 3. The length of a distal-end stiff portion is thereby as shown in Table 1.

After the coil spring was installed on the core wire, a cured resin (urethane-acrylate resin) was filled into the interior of the coil spring, a resin layer by the cured resin was formed on an outer periphery of the coil spring, and a hydrophilic resin layer composed of polyethylene oxide was laminated and formed on the surface of this resin layer.

(2) Evaluation of Guide Wire

With respect to each of the 13 guide wires obtained in the above item (1), a minimum shaping length (minimum length capable of being bent) was measured.

The measurement of the minimum shaping length was conducted on an inside length ($L_{51}$) and an outside length ($L_{52}$) as illustrated in FIG. 4.

Tensile force was applied between the coil spring and the core wire to observe a broken site, thereby evaluating the fixing ability of the coil spring to the core wire. With respect to the evaluation standard, the guide wires were ranked as "A" where breaking occurred at the distal end-side small-diameter portion of the core wire or "B" where separation occurred between the coil spring or the distal end-side small-diameter portion and the solder. When even one guide wire was ranked as "B", their guide wires cannot be provided as products. The results are shown collectively in Table 1.

TABLE 1

|  | Run No. | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|---|
|  |  |  |  |  | Inside length ($L_{51}$) | Outside length ($L_{52}$) |  |
| Example 1 | 1 | Au—Sn | 2 | 0.3-0.4 | 0.32 | 0.53 | A |
|  | 2 | Au—Sn | 2 | 0.3-0.4 | 0.31 | 0.51 | A |
|  | 3 | Au—Sn | 1 | 0.1-0.3 | 0.13 | 0.35 | A |
|  | 4 | Au—Sn | 3 | 0.4-0.5 | 0.42 | 0.63 | A |
|  | 5 | Au—Sn | 2 | 0.3-0.4 | 0.33 | 0.55 | A |
|  | 6 | Au—Sn | 1 | 0.1-0.3 | 0.12 | 0.32 | A |
|  | 7 | Au—Sn | 2 | 0.3-0.4 | 0.30 | 0.51 | A |
|  | 8 | Au—Sn | 1 | 0.1-0.3 | 0.11 | 0.29 | A |
|  | 9 | Au—Sn | 1 | 0.1-0.3 | 0.14 | 0.32 | A |
|  | 10 | Au—Sn | 3 | 0.4-0.5 | 0.43 | 0.65 | A |
|  | 11 | Au—Sn | 3 | 0.4-0.5 | 0.44 | 0.68 | A |
|  | 12 | Au—Sn | 2 | 0.3-0.4 | 0.32 | 0.53 | A |
|  | 13 | Au—Sn | 1 | 0.1-0.3 | 0.12 | 0.32 | A |

Example 2

Thirteen guide wires of such a structure as illustrated in FIG. 1 to FIG. 3 according to the present invention were prepared in the same manner as in Example 1 except that Au—Ge solder was used as the solder for fixing the front end portion and intermediate portion of the coil spring to the core wire, and Ag—Sn solder was used as the solder for fixing the rear end portion of the coil spring to the core wire.

In each of the 13 guide wires, the number (in Table 2, abbreviated as "Number of pitches") of pitches at a coil portion corresponding to a region (length) where the solder penetrated into the interior thereof was set to any of 1 to 3. The length of a distal-end stiff portion is thereby as shown in Table 2.

After the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the 13 guide wires obtained in the above-described manner, a minimum shaping length was measured in the same manner as in Example 1, thereby evaluating the fixing ability. The results are shown collectively in Table 2.

Comparative Example 1

Ag—Sn solder was used as solder for fixing the front end portion, intermediate portion and rear end portion of a coil spring to a core wire to prepare 13 comparative guide wires.

In each of the 13 guide wires, the number (in Table 3, abbreviated as "Number of pitches") of pitches at a coil portion corresponding to a region (length) where the solder penetrated into the interior thereof was set to any of 1 to 3. The length of a distal-end stiff portion is thereby as shown in Table 3.

After the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the 13 guide wires obtained in the above-described manner, a minimum shaping length was measured in the same manner as in Example 1, thereby evaluating the fixing ability. The results are shown collectively in Table 3.

This Comparative Example 1 is a comparative example where no gold-containing solder was used upon fixing the front end portion of the coil spring to the core wire.

TABLE 2

|  | Run. No. | Kind of solder used in fixing of front end portion and intermediate portion | Number of pitches | Length of distal-end stiff portion [mm] | Minimum shaping length [mm] | | Evaluation of fixing ability |
| --- | --- | --- | --- | --- | --- | --- | --- |
|  |  |  |  |  | Inside length ($L_{51}$) | Outside length ($L_{52}$) |  |
| Example 2 | 1 | Au—Ge | 2 | 0.3-0.4 | 0.31 | 0.52 | A |
|  | 2 | Au—Ge | 3 | 0.4-0.5 | 0.42 | 0.62 | A |
|  | 3 | Au—Ge | 2 | 0.3-0.4 | 0.32 | 0.54 | A |
|  | 4 | Au—Ge | 2 | 0.3-0.4 | 0.33 | 0.53 | A |
|  | 5 | Au—Ge | 3 | 0.4-0.5 | 0.44 | 0.67 | A |
|  | 6 | Au—Ge | 1 | 0.1-0.3 | 0.11 | 0.30 | A |
|  | 7 | Au—Ge | 3 | 0.4-0.5 | 0.43 | 0.64 | A |
|  | 8 | Au—Ge | 1 | 0.1-0.3 | 0.12 | 0.29 | A |
|  | 9 | Au—Ge | 2 | 0.3-0.4 | 0.30 | 0.52 | A |
|  | 10 | Au—Ge | 1 | 0.1-0.3 | 0.12 | 0.34 | A |
|  | 11 | Au—Ge | 2 | 0.3-0.4 | 0.33 | 0.53 | A |
|  | 12 | Au—Ge | 1 | 0.1-0.3 | 0.14 | 0.31 | A |
|  | 13 | Au—Ge | 1 | 0.1-0.3 | 0.12 | 0.31 | A |

TABLE 3

| | Run No. | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|---|
| | | | | | Inside length ($L_{51}$) | Outside length ($L_{52}$) | |
| Comparative Example 1 | 1 | Ag—Sn | 2 | 0.3-0.4 | 0.31 | 0.52 | A |
| | 2 | Ag—Sn | 1 | 0.1-0.3 | 0.11 | 0.29 | B |
| | 3 | Ag—Sn | 1 | 0.1-0.3 | 0.14 | 0.32 | B |
| | 4 | Ag—Sn | 2 | 0.3-0.4 | 0.32 | 0.53 | A |
| | 5 | Ag—Sn | 3 | 0.4-0.5 | 0.44 | 0.68 | A |
| | 6 | Ag—Sn | 3 | 0.4-0.5 | 0.42 | 0.66 | B |
| | 7 | Ag—Sn | 2 | 0.3-0.4 | 0.30 | 0.53 | A |
| | 8 | Ag—Sn | 3 | 0.4-0.5 | 0.40 | 0.62 | A |
| | 9 | Ag—Sn | 3 | 0.4-0.5 | 0.45 | 0.69 | A |
| | 10 | Ag—Sn | 2 | 0.3-0.4 | 0.34 | 0.54 | A |
| | 11 | Ag—Sn | 1 | 0.1-0.3 | 0.12 | 0.34 | B |
| | 12 | Ag—Sn | 2 | 0.3-0.4 | 0.33 | 0.52 | B |
| | 13 | Ag—Sn | 2 | 0.3-0.4 | 0.35 | 0.56 | A |

Comparative Examples 2 to 6

Ag—Sn solder was used as solder for fixing the front end portion, intermediate portion and rear end portion of a coil spring to a core wire to prepare comparative guide wires the lengths of distal-end stiff portions of which exceeded 0.5 mm.

In each of the guide wires, the number (in Table 4, abbreviated as "Number of pitches") of pitches at a coil portion corresponding to a region (length) where the solder penetrated into the interior thereof was set to any of 4 to 8. The length of a distal-end stiff portion is thereby as shown in Table 4.

After the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the guide wires obtained in the above-described manner, a minimum shaping length was measured in the same manner as in Example 1. The results are shown collectively in Table 4.

Examples 3 to 5

Any of Au—Si solder, Au—In solder and Au—Sb solder was used as the solder for fixing the front end portion and intermediate portion of a coil spring to a core wire, and Ag—Sn solder was used as the solder for fixing the rear end portion of the coil spring to the core wire, thereby preparing 9 guide wires (3 guide wires in each Example) according to the present invention. In each of the guide wires thus obtained, the number (in Table 5, abbreviated as "Number of pitches") of pitches at a coil portion corresponding to a region (length) where the solder penetrated into the interior thereof was set to any of 1 to 3. The length of a distal-end stiff portion is thereby as shown in Table 5.

After the coil spring was installed on the core wire, in the same manner as in Example 1, the cured resin was filled into the interior of the coil spring, the resin layer by the cured resin was formed on an outer periphery of the coil spring, and the hydrophilic resin layer was laminated and formed on the surface of this resin layer.

With respect to each of the 9 guide wires obtained in the above-described manner, a minimum shaping length was

TABLE 4

| | Kind of solder used in fixing of front end portion and intermediate portion | Number of pitches | Length of distal-end stiff portion [mm] | Minimum shaping length [mm] | |
|---|---|---|---|---|---|
| | | | | Inside length ($L_{51}$) | Outside length ($L_{52}$) |
| Comp. Ex. 2 | Ag—Sn | 4 | 0.6-0.7 | 0.62 | 0.81 |
| Comp. Ex. 3 | Ag—Sn | 5 | 0.7-0.8 | 0.74 | 0.90 |
| Comp. Ex. 4 | Ag—Sn | 6 | 0.8-0.9 | 0.82 | 1.01 |
| Comp. Ex. 5 | Ag—Sn | 7 | 0.9-1.0 | 0.94 | 1.14 |
| Comp. Ex. 6 | Ag—Sn | 8 | 1.0-1.1 | 1.03 | 1.21 | measured in the same manner as in Example 1, thereby evaluating the fixing ability. The results are shown collectively in Table 5.

TABLE 5

| | Kind of solder used in fixing of front end portion and intermediate portion | Number of pitches | Length of distal-end stiff portion [mm] | Minimum shaping length [mm] | | Evaluation of fixing ability |
|---|---|---|---|---|---|---|
| | | | | Inside length ($L_{S1}$) | Outside length ($L_{S2}$) | |
| Ex. 3 | Au—Si | 1 | 0.1-0.3 | 0.12 | 0.33 | A |
| | Au—Si | 2 | 0.3-0.4 | 0.31 | 0.53 | A |
| | Au—Si | 3 | 0.4-0.5 | 0.43 | 0.65 | A |
| Ex. 4 | Au—In | 1 | 0.1-0.3 | 0.11 | 0.31 | A |
| | Au—In | 2 | 0.3-0.4 | 0.32 | 0.54 | A |
| | Au—In | 3 | 0.4-0.5 | 0.44 | 0.66 | A |
| Ex. 5 | Au—Sb | 1 | 0.1-0.3 | 0.11 | 0.28 | A |
| | Au—Sb | 2 | 0.3-0.4 | 0.33 | 0.53 | A |
| | Au—Sb | 3 | 0.4-0.5 | 0.43 | 0.64 | A |

REFERENCE SIGNS LIST

10 Core wire
11 Distal end-side small-diameter portion
13 Tapered portion
14 Proximal end-side large-diameter portion
20 Coil spring
21 Front end-side densely-coiled portion
22 Rear end-side roughly-coiled portion
31 Au—Sn solder
32 Au—Sn solder
33 Ag—Sn solder
40 Cured resin
40A Resin layer
50 Hydrophilic resin layer

The invention claimed is:

1. A medical guide wire comprising
a core wire having a distal end-side small-diameter section and a proximal end-side large-diameter section, the proximal end-side large-diameter section having a larger outside diameter than the outside diameter of the distal end-side small-diameter section, and
a coil spring installed on an outer periphery of the distal end-side small-diameter section of the core wire along an axial direction and fixed to the core wire at least at a front end portion and a rear end portion thereof, wherein
the outside diameter of the proximal end-side large-diameter section of the core wire and the outside diameter of a coil of the coil spring are each at most 0.012 inch,
the front end portion of the coil spring is fixed to the core wire at a first location by a gold-containing solder,
a length of a distal end portion of the guide wire which is stiffened by the gold-containing solder is 0.1 to 0.5 mm,
the distal end-side small-diameter section and the proximal end-side large-diameter section are integrally formed of the same wire member,
the distal end-side small-diameter section has a tapered portion,
the coil spring is composed of a front end-side densely-coiled portion whose coil pitch is 1.0 to 1.8 times as much as the wire diameter of the coil, and a rear end-side roughly-coiled portion whose coil pitch exceeds 1.8 times as much as the wire diameter of the coil, and
an intermediate portion of the coil spring, including the front end-side densely-coiled portion and the rear end-side roughly-coiled portion, is fixed to the core wire at a second location by the gold-containing solder.

2. The medical guide wire according to claim 1, which further comprises a tapered section which is disposed between the distal end-side small-diameter section and the proximal end-side large-diameter section, wherein the tapered section is integrally formed of the same wire member as the distal end-side small-diameter section and the proximal end-side large-diameter section.

3. The medical guide wire according to claim 1, wherein the outside diameter of the proximal end-side large-diameter portion of the core wire and the outside diameter of coil of the coil spring are each at most 0.010 inch; the solder penetrates into the interior of the coil in a range corresponding to 1 to 3 pitches of the coil spring; a resin is disposed into the interior of the coil spring, thereby a resin layer is formed on the outer periphery of the coil spring, a hydrophilic resin layer is laminated and formed on the surface of the resin layer, and a water-repellent resin layer is formed on the surface of the core wire; the coil spring includes a front end-side densely-coiled portion whose coil pitch is 1.0 to 1.8 times as much as the wire diameter of the coil, and a rear end-side roughly-coiled portion whose coil pitch exceeds 1.8 times as much as the wire diameter of the coil; and an intermediate portion of the coil spring, including the front end-side densely-coiled portion and the rear end-side roughly-coiled portion, is fixed to the core wire by the solder.

4. A medical guide wire comprising
a core wire having a distal end-side small-diameter section and a proximal end-side large-diameter section, the proximal end-side large-diameter section having a larger outside diameter than the outside diameter of the distal end-side small-diameter section, and
a coil spring installed on an outer periphery of the distal end-side small-diameter section of the core wire along an axial direction and fixed to the core wire at least at a front end portion and a rear end portion thereof, wherein
the outside diameter of the proximal end-side large-diameter section of the core wire and the outside diameter of a coil of the coil spring are each at most 0.012 inch,
the front end portion of the coil spring is fixed to the core wire at a first location by a Au—Sn solder,
a length of a distal end portion of the guide wire which is stiffened by the Au—Sn solder is 0.1 to 0.5 mm,
the distal end-side small-diameter section and the proximal end-side large diameter section are integrally formed of the same wire member,
the distal end-side small-diameter section has a tapered portion,
the coil spring is composed of a front end-side densely-coiled portion whose coil pitch is 1.0 to 1.8 times as much as the wire diameter of the coil, and a rear end-side roughly-coiled portion whose coil pitch exceeds 1.8 times as much as the wire diameter of the coil, and
an intermediate portion of the coil spring, including the front end-side densely-coiled portion and the rear end-side roughly-coiled portion, is fixed to the core wire at a second location by the Au—Sn solder.

5. The medical guide wire according to claim 4, wherein the outside diameter of the proximal end-side large-diameter portion of the core wire and the outside diameter of coil of the coil spring are each at most 0.010 inch.

6. The medical guide wire according to claim 4, wherein the coil pitch of the coil spring at its front end portion is 1.0 to 1.8 times as much as the wire diameter of the coil, and
   the Au—Sn solder penetrates into the interior of the coil in a range corresponding to 1 to 3 pitches of the coil spring.

7. The medical guide wire according to claim 4, wherein a resin is filled into the interior of the coil spring, thereby a resin layer is formed on the outer periphery of the coil spring, a hydrophilic resin layer is laminated and formed on the surface of the resin layer, and
   a water-repellent resin layer is formed on the surface of the core wire.

8. The medical guide wire according to claim 4, wherein the core wire is composed of stainless steel.

9. The medical guide wire according to claim 4, which further comprises a tapered section which is disposed between the distal end-side small-diameter section and the proximal end-side large-diameter section, wherein the tapered section is integrally formed of the same wire member as the distal end-side small-diameter section and the proximal end-side large-diameter section.

10. A medical guide wire comprising a core wire having a distal end-side small-diameter section and a proximal end-side large-diameter section, the proximal end-side large-diameter section having a larger outside diameter than the outside diameter of the distal end-side small-diameter section, and
   a coil spring installed on an outer periphery of the distal end-side small-diameter section of the core wire along an axial direction and fixed to the core wire at least at a front end portion and a rear end portion thereof, wherein
   the outside diameter of the proximal end-side large-diameter section of the core wire and the outside diameter of a coil of the coil spring are each at most 0.012 inch,
   the front end portion of the coil spring is fixed to the core wire at a first location by a Au—Ge solder,
   a length of a distal end portion of the guide wire which is stiffened by the Au—Ge solder is 0.1 to 0.5 mm,
   the distal end-side small-diameter section and the proximal end-side large-diameter section are integrally formed of the same wire member,
   the distal end-side small-diameter section has a tapered portion,
   the coil spring is composed of a front end-side densely-coiled portion whose coil pitch is 1.0 to 1.8 times as much as the wire diameter of the coil, and a rear end-side roughly-coiled portion whose coil pitch exceeds 1.8 times as much as the wire diameter of the coil, and
   an intermediate portion of the coil spring, including the front end-side densely-coiled portion and the rear end-side roughly-coiled portion, is fixed to the core wire at a second location by the Au—Ge solder.

11. The medical guide wire according to claim 10, wherein the outside diameter of the proximal end-side large-diameter portion of the core wire and the outside diameter of coil of the coil spring are each at most 0.10 inch.

12. The medical guide wire according to claim 10, wherein the coil pitch of the coil spring at its front end portion is 1.0 to 1.8 times as much as the wire diameter of the coil, and
   the Au—Ge solder penetrates into the interior of the coil in a range corresponding to 1 to 3 pitches of the coil spring.

13. The medical guide wire according to claim 10, wherein a resin is filled into the interior of the coil spring, thereby a resin layer is formed on the outer periphery of the coil spring, a hydrophilic resin layer is laminated and formed on the surface of the resin layer, and
   a water-repellent resin layer is formed on the surface of the core wire.

14. The medical guide wire according to claim 10, wherein the core wire is composed of stainless steel.

15. The medical guide wire according to claim 10, which further comprises a tapered section which is disposed between the distal end-side small-diameter section and the proximal end-side large-diameter section, wherein the tapered section is integrally formed of the same wire member as the distal end-side small-diameter section and the proximal end-side large-diameter section.

* * * * *